United States Patent [19]

Varaprath

[11] Patent Number: 4,608,270

[45] Date of Patent: Aug. 26, 1986

[54] ACYLAMINO SILICON COMPOUNDS, THEIR USE AND PREPARATION

[75] Inventor: Padmakumari J. Varaprath, Midland, Mich.

[73] Assignee: Dow Corning Corporation, Midland, Mich.

[21] Appl. No.: 791,484

[22] Filed: Oct. 25, 1985

[51] Int. Cl.$^4$ ............................................. B05D 3/06
[52] U.S. Cl. ................................... 427/35; 427/54.1; 428/447; 428/452; 556/419; 556/424; 528/25; 528/26; 522/99
[58] Field of Search ................... 556/419, 424; 528/25, 528/26; 427/54.1, 35; 428/447, 452; 522/99

[56] References Cited

U.S. PATENT DOCUMENTS

| | | | |
|---|---|---|---|
| 2,929,829 | 3/1960 | Morehouse | 260/448.2 |
| 4,075,167 | 2/1978 | Takamizawa et al. | 260/46.5 E |
| 4,293,397 | 10/1981 | Sato et al. | 522/99 |
| 4,507,455 | 3/1985 | Tangney et al. | 528/26 |
| 4,543,398 | 9/1985 | Bany et al. | 556/419 |

FOREIGN PATENT DOCUMENTS 56-74113 6/1981 Japan.

Primary Examiner—Melvyn I. Marquis
Attorney, Agent, or Firm—George A. Grindahl

[57] ABSTRACT

Organosilicon compounds containing at least one acylamino-substituted hydrocarbon radical are prepared by reacting an organosilicon compound containing at least one amino-substituted hydrocarbon radical with an acyl halide in the presence of an aqueous solution of an alkaline material and a solvent for the aminosilicon compound. The reaction is particularly useful for preparing polydiorganosiloxanes which contain one or more acrylylamino-substituted hydrocarbon radicals, which are polymerizable and are useful in coating compositions such as adhesive release coating compositions.

35 Claims, No Drawings

ACYLAMINO SILICON COMPOUNDS, THEIR USE AND PREPARATION

BACKGROUND OF THE INVENTION

This invention relates generally to a method for preparing organosilicon compounds which contain silicon-bonded acylamino-substituted hydrocarbon radicals, to organosilicon compounds obtained therefrom, to curable coating compositions comprising the organosilicon compounds and to a process for providing a substrate with a coating of a cured organosilicon compound. In a preferred embodiment this invention relates to organosilicon compounds bearing silicon-bonded acrylylamino-substituted hydrocarbon radicals.

Organosilicon compounds which contain silicon-bonded acylamino-substituted hydrocarbon radicals, are well known.

U.S. Pat. No. 2,929,829 to Morehouse teaches that organosilicon compounds containing an acylamino group which is attached to a silicon atom through a polymethylene linkage that contains at least three carbon atoms can be prepared by the reaction of an organosilicon compound bearing an aminoalkyl group with a monocarboxylic acid or an ester, halide or anhydride thereof. In the case of monocarboxylic acid halides the reaction is typically conducted in the presence of a hydrogen halide scavenger such as triethylamine. It is well known that the byproduced amine hydrohalide salt is frequently difficult to handle and remove completely from the desired product.

U.S. Pat. No. 4,507,455 to Tangney and Ziemelis teaches that organosilicon compounds that contain acylated N-(aminohydrocarbyl)-aminohydrocarbyl radicals can be prepared by a process which comprise mixing a monocarboxylic acid anhydride with an organosilicon compound which contains N-(aminohydrocarbyl)-aminohydrocarbyl radicals. However, in this process, the desired product is usually isolated by a vacuum distillation step which cannot be used on temperature sensitive compounds such as those containing acrylylated amino-substituted hydrocarbon radicals.

Japanese O.P.I. No. 74113/81 to Takamizawa, et al. discloses photosetting organopolysiloxane compositions which comprise an organopolysiloxane bearing acylamino-substituted hydrocarbon radicals which contain unsaturation and are photopolymerizable. The photopolymerizable organopolysiloxane is produced by the method of Morehouse and has the shortcomings noted above. In addition, even in the presence of a large excess of a tertiary amine such as triethylamine, pyridine, or quinoline to take up hydrogen chloride, some addition of HCl across the double bond of an acrylyl chloride is known to occur, leading to the formation of chloropropionic acids and a corresponding loss of acrylyl activity.

U.S. Pat. No. 4,075,167 to Takamizawa, et al. discloses maleimido group-containing organosilicon compounds which are photocurable. While this method provides fully acylated products from organosilicon compounds which contain monoaminohydrocarbyl radicals, such is not the case with organosilicon compounds which contain N-(aminohydrocarbyl)-aminohydrocarbyl radicals. In the latter case either the secondary amine hydrogen is not acylated or, if it is, an unreacted carboxyl radical from the maleimide reaction remains in the product.

In view of the extensive interest in photocurable organosilicon compounds it would be beneficial to have new and improved methods for the preparation of acrylylamine-substituted organosilicon compounds.

BRIEF SUMMARY OF THE INVENTION

It is an object of this invention to provide organosilicon compounds which contain one or more fully acrylylated silicon-bonded N-(aminohydrocarbyl)-aminohydrocarbyl radicals, herein also designated acrylylated diamine radicals. It is a particular object of this invention to provide organopolysiloxane compounds which contain at least one fully acrylylated silicon-bonded diamine radical. It is also an object of this invention to provide a method for preparing organosilicon compounds which contain at least one silicon-bonded acylamino-substituted hydrocarbon radical. It is a further object of this invention to provide curable organosilicon compositions and a process for providing a cured silicon-containing coating on a substrate.

These objects, and others which may become apparent upon consideration of the following disclosure and appended claims, are obtained by this invention which comprises reacting an organosilicon compound containing at least one acylatable silicon-bonded amine-substituted hydrocarbon radical with an acyl halide in an aqueous alkaline system. When the acyl halide is an acrylyl halide the present invention readily provides organosilicon compounds containing acrylylamine-substituted hydrocarbon radicals without many of the problems associated with the methods of the art, noted above. When the amine-containing organosilicon compound is one which comprises one or more diamine radicals the method of this invention provides novel organosilicon compounds containing fully acrylylated diamine radicals. The acrylylated organosilicon compounds of this invention find particular utility as reactive components in curable compositions.

Herein terms having the root acryl, such as acrylyl, acrylylate, acrylylated and acrylylamide, denote the

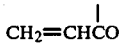

structure and/or the

structure unless otherwise indicated.

DETAILED DESCRIPTION OF THE INVENTION

In a first aspect the present invention relates to an organosilicon compound containing at least one silicon-bonded acylamino-substituted hydrocarbon radical having the formula —QNAQ'NAZ, wherein Z denotes H or R, R denotes a monovalent hydrocarbon radical, Q and Q' denote divalent hydrocarbon radicals, A denotes an acyl radical having the formula

and B denotes H or $CH_3$, any remaining silicon-bonded radicals therein being selected from the group consisting of organic radicals and divalent oxygen atoms linking silicon atoms.

The organosilicon compounds of this invention can have any structure provided that they contain at least one silicon atom having bonded thereto a hydrocarbon radical that bears a fully acrylylated diamine group, hereinafter delineated, and any other silicon bonds are satisfied by organic radicals, other than the acrylylamino-substituted hydrocarbon radicals noted above, and divalent oxygen atoms linking silicon atoms.

Thus the compounds of this invention include silanes, siloxanes, silcarbanes and silcarbanesiloxanes.

The silicon-bonded acylamino-substituted hydrocarbon radical has the formula —QNAQ'NAZ, wherein Q and Q' denote divalent hydrocarbon radicals, Z denotes a hydrogen atom or a monovalent hydrocarbon radical, i.e. R radical, and A denotes an acyl radical having the formula $$CH_2{=}CBCO.$$

Examples of Q radicals and Q' radicals include, but are not limited to, alkylene radicals such as —$CH_2CH_2$—,

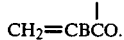

—$CH_2CH_2CH_2$—, —$CH_2CH(CH_3)CH_2$—, and —$(CH_2)_6$—; and arylene radicals such as —$C_6H_4$—, —$CH_2C_6H_4$— and $CH_2C_6H_4CH_2$—.

Examples of hydrocarbon Z radicals (R radicals) include, but are not limited to, alkyl radicals such as methyl, ethyl, propyl, butyl, hexyl and octyl; cycloaliphatic radicals such as cyclohexyl; aryl radicals such as phenyl, benzyl, styryl, tolyl and xenyl; and alkenyl radicals such as vinyl and allyl.

In a preferred embodiment the compounds of this invention are prepared from silicon-containing precursors that have been prepared from ethylene diamine and a suitable silicon compound and thus contain silicon-bonded diamine radicals of the formula —$QNHCH_2CH_2NH_2$. Therefore, in the compounds of this invention Z preferably denotes H and Q' preferably denotes —$CH_2CH_2$—.

Q can be the same as, or different from, Q' in the compounds of this invention. Preferably Q is an alkylene radical having from 3 to 10 carbon atoms and there are at least 3 carbon atoms between the silicon atom and the nitrogen bonded to the Q radical. An example of a preferred Q radical is —$CH_2CH(CH_3)CH_2$—.

In the compounds of this invention A denotes an acyl radical having the formula

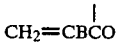

wherein B denotes H or $CH_3$, i.e., an acryIyl radical or a methacrylyl radical.

Examples of acrylylamino-substituted hydrocarbon radicals include, but are not limited to,

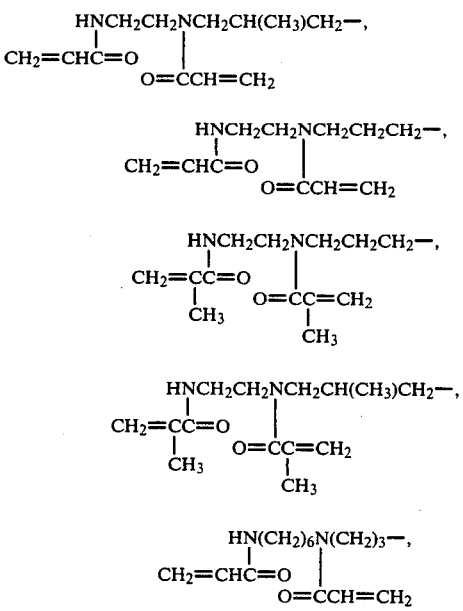

Silicon-bonded radicals, other than the above-noted acrylylamino-substituted hydrocarbon radicals, include organic radicals and divalent oxygen atoms linking silicon atoms. Examples of said organic radicals include, but are not limited to, divalent hydrocarbon radicals linking silicon atoms such as Q and Q' radicals noted above, and halogenated derivatives thereof; monovalent hydrocarbon radicals such as R radicals noted above, and halogen derivatives thereof; hydrogen atoms, hydroxy radicals, —OA radicals and alkoxy radicals such as methoxy radicals. Preferably said organic radicals contain no more than 6 carbon atoms, such as methyl, 3,3,3-trifluoropropyl, phenyl and vinyl radicals. For most applications of the compounds of this invention the organic radicals are methyl radicals.

The compounds of this invention are preferably silanes or siloxanes having the average unit formula $$R_c(NAHQ'NAQ)_d SiO_{(4-c-d)/2}$$

wherein c denotes a number having a value of from 0 to 3, such as 0, 0.5, 1.01, 2, 2.1 and 3, d denotes a number having a value of from >0 to 4, such as 0.01, 0.5, 1, 2 and 3, and c+d has a value of from 1 to 4 such as 1.5, 1.99, 2.01, 3 and 4. Of course, as noted above, the silane or siloxane compounds of this invention must contain an average of at least one fully acrylylated silicon-bonded diamine radical per molecule. The siloxanes can contain siloxane units which are free of acrylylamino-substituted hydrocarbon radicals such as $R_cSiO_{(4-c)/2}$ such as $MeSiO_{3/2}$, $Me_2SiO_{2/2}$, $MeViSiO_{2/2}$, $MePhSiO_{2/2}$, $Me_3SiO_{1/2}$, $Me_2(OA)SiO_{1/2}$, $ViMe_2SiO_{1/2}$ and $SiO_{4/2}$ units, in addition to siloxane unit which contain the required acylamino-substituted hydrocarbon radicals. The siloxane of this invention can also contain partially acrylated diamine radicals such as $NAHCH_2CH_2NHCH_2CH(CH_3)CH_2Si(CH_3)O_{2/2}$.

Preferred silanes of this invention have the formula $(R)_eSi(QNACH_2CH_2NAH)_{4-e}$ wherein e denotes a number having a value of 0, 1, 2 or 3, such as

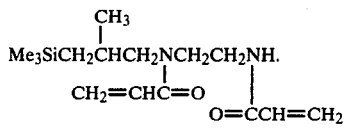

Preferred siloxanes of this invention have the formula $YR_2SiO(R_2SiO)_x(YRSiO)_ySiR_2Y$ wherein each Y denotes, independently, an R radical or a $-QNACH_2CH_2NAH$ radical and x and y denote numbers having average values of from 0 to 5000 and 0 to 500, respectively. Examples of preferred siloxanes of this invention include, but are not limited to,
$Me_3SiO(Me_2SiO)_{500}(MeYSiO)_2SiMe_3$,
$YMe_2SiO(Me_2SiO)_{2000}SiMe_2Y$,
$YMe_2SiO(Me_2SiO)_{100}(MeYSiO)_3SiMe_2Y$,
$Me_3SiO(MeYSiO)_1SiMe_3$ and
$YMe_2SiO(MeYSiO)_1SiMe_2Y$.

Siloxanes of this invention can also have a cyclic or branched structure such as $(YMe_2SiO)_4Si$ and $(YMeSiO)_4$, in addition to the linear structure noted above.

Further examples of the compounds of this invention are disclosed in the discussion of the method of their preparation, of their use in the curable compositions of this invention, of the process of coating a substrate and in the examples noted below.

Herein the symbols Me, Ph and Vi denote methyl, phenyl and vinyl, respectively.

The organosilicon compounds of this invention can be prepared by the method of this invention. While the method of this invention was developed specifically for the preparation of the compounds of this invention it has been found to have general utility for the preparation of organosilicon compounds containing any silicon-bonded acylamine-substituted hydrocarbon radical.

Thus, in a second aspect, this invention relates to a method for preparing an organosilicon compound containing at least one silicon-bonded acylamino-substituted hydrocarbon radical, said method comprising (I) admixing (i) a composition comprising an acyl halide to (ii) a composition comprising an aminosilicon compound having at least one silicon-bonded amino-substituted hydrocarbon radical containing at least one nitrogen-bonded hydrogen, all other silicon valences therein being satisfied by radicals selected from the group consisting of organic radicals and divalent oxygen atoms linking silicon atoms, said admixing being done in the presence of (iii) an aqueous solution of a water-soluble alkaline material and (iv) a water-insoluble solvent for (ii), the amounts of components (i), (ii) and (iii) being sufficient to acylate at least one amino nitrogen atom containing at least one nitrogen-bonded hydrogen atom per molecule of aminosilicon compound and to provide at least an equivalent amount of alkaline material relative to the amount of acyl halide, and thereafter (II) agitating the mixture comprising (i) and (ii) until the compound is formed.

In the method of this invention the acyl halide that is used can have any structure such as a linear, branched or cyclic structure having aromatic, heterocyclic, olefinic or paraffinic bonding and containing one or more carbon-bonded $-COX$ radicals, wherein X denotes a halogen atom. Preferably the acyl halide has the structure R"COX wherein X denotes a halogen atom, preferably chlorine, and R" denotes a substituted or unsubstituted monovalent hydrocarbon radical.

Examples of unsubstituted R" radicals include, but are not limited to, those delineated above for hydrocarbon radicals (R radicals). Examples of corresponding acyl halides thus include acetyl chloride, benzoyl chloride and, most preferably, acrylyl chloride and methacrylyl chloride.

Examples of substituted R" radicals include, but are not limited to, halogenated R radicals such as $-CF_3$ and $-C_6H_4Cl$, and other substituted radicals which are stable under the reaction conditions employed in the method of this invention such as $-CH_2CH_2CN$, $-C_6H_4NO_2$ and $-C(CN)=CH_2$.

In the method of this invention the aminosilicon compound that is to be acylated can have any structure as long as it contains at least one silicon atom having bonded thereto an amino-substituted hydrocarbon radical that bears one or more amino radicals, at least one of which bears a nitrogen-bonded hydrogen atom, and any other silicon bonds are satisfied by organic radicals, other than the amine radicals noted above, and divalent oxygen atoms linking silicon atoms. Thus the aminosilicon compound can be a silane, a siloxane, a silcarbane or a silcarbanesiloxane.

The silicon-bonded amino-substituted hydrocarbon radical has the formula $-Q(NHQ')_aNHZ$ wherein Q, Q' and Z have the general and preferred meanings denoted above for the compounds of this invention and a has a value of 0 or 1.

Examples of amino-substituted hydrocarbon radicals include, but are not limited to,
$NH_2CH_2CH_2CH_2-$, $CH_3NHCH_2CH_2CH_2-$,
$NH_2CH_2CH(CH_3)CH_2-$,
$NH_2CH_2CH_2NHCH_2CH_2CH_2-$,
$NH_2CH_2CH_2NHCH_2CH(CH_3)CH_2-$,
$NH_2(CH_2)_6NH(CH_2)_3-$ and
$NH_2(CH_2)_6NHCH_2CH(CH_3)CH_2-$.

Silicon-bonded radicals, other than the above-noted amino-substituted hydrocarbon radicals, include organic radicals and divalent oxygen atoms linking silicon atoms. Examples of said organic radicals include, but are not limited to, divalent hydrocarbon radicals linking silicon atoms such as Q and Q' radicals noted above, and halogenated derivatives thereof, monovalent hydrocarbon radicals such as R radicals noted above, and halogenated derivatives thereof, alkoxy radicals such as methoxy radicals, hydroxy radicals, $-OA$ radicals and hydrogen atoms. Preferably said organic radicals contain no more than 6 carbon atoms, such as methyl, 3,3,3-trifluoropropyl, phenyl and vinyl radicals, and most preferably are methyl radicals.

The aminosilicon compounds to be acylated by the process of this invention are preferably silanes or siloxanes having the average formula 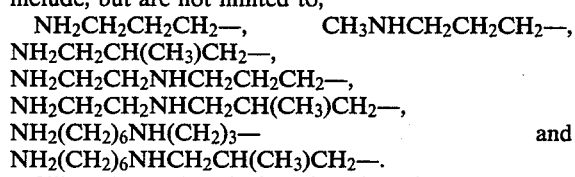 wherein c denotes a number having a value of from 0 to 3, such as 0, 0.5, 1.01, 2, 2.1 and 3, d denotes a number having a value of from >0 to 4, such as 0.01, 0.5, 1, 2 and 3, and c+d has a value of from 1 to 4 such as 1.5, 1.99, 2.01, 3 and 4. Of course, the aminosilane or siloxane must contain an average of at least one silicon-bonded, amine-substituted hydrocarbon radical per molecule. The siloxanes can contain siloxane unit which are free of amino-substituted hydrocarbon radicals such as $R_cSiO_{(4-c)/2}$ such as $MeSiO_{3/2}$, $Me_2SiO_{2/2}$, $Me_3SiO_{1/2}$, $MeViSiO_{2/2}$, $MePhSiO_{2/2}$, $Me_2(OA)SiO_{1/2}$, $ViMe_2SiO_{1/2}$ and $SiO_{4/2}$ units, in addition to siloxane unit which contain the required amino-substituted hydrocarbon radicals.

Preferred aminosilanes to be acylated have the formula $(R)_e Si(QNHCH_2CH_2NH_2)_{4-e}$ wherein e denotes a number having a value of 0, 1, 2 or 3, such as $Me_3SiCH_2CH(CH_3)CH_2NHCH_2CH_2NH_2$.

Preferred aminosiloxanes to be acylated have the formula $Y'R_2SiO(R_2SiO)_x(Y'RSiO)_ySiR_2Y'$ wherein each Y' denotes, independently, an R radical or a $-QNHCH_2CH_2NH_2$ radical and x and y denote numbers having average values of from 0 to 5000 and 0 to 500, respectively. Examples of preferred aminosiloxanes to be acylated include, but are not limited to, $Me_3SiO(Me_2SiO)_{500}(MeY'SiO)_2SiMe_3$, $Y'Me_2SiO(Me_2SiO)_{2000}SiMe_2Y'$, $Y'Me_2SiO(Me_2SiO)_{100}(MeY'SiO)_3SiMe_2Y'$, $Me_3SiO(MeY'SiO)_1SiMe_3$ and $Y'Me_2SiO(MeY'SiO)_1SiMe_2Y'$ Aminosiloxanes can also have a cyclic or branched structure such as $(Y'Me_2SiO)_4Si$ and $(Y'MeSiO)_4$, in addition to the linear structure noted above.

Further examples of the aminosilicon compounds that can be acylated by the method of this invention are disclosed in the examples noted below.

Aminosilicon compounds are well known in the organosilicon art and need no detailed description herein as to their preparation. Some are commercially available. The disclosures of U.S. Pat. Nos. 2,557,803; 2,738,357; 2,754,312; 2,762,823; 2,998,406; 3,045,036; 3,087,909; 3,355,424; 3,560,543; 3,890,269; 4,036,868; 4,152,346 and 4,507,455 are incorporated herein by reference to further teach how to prepare aminosilicon compounds that can be used in the method of this invention.

In the method of this invention the acyl halide is admixed to the aminosilicon compound in the presence of an aqueous solution of an alkaline material. The alkaline material can be any water-soluble material having a pKb value greater than the pKb of the amine radicals in the amino-substituted hydrocarbon radicals to be acylated. The alkaline material is preferably an alkali metal hydroxide such as sodium hydroxide or potassium hydroxide.

In addition to the aqueous solution of alkaline material, there is also present a water-insoluble solvent for the aminosilicon when the acyl halide is admixed to the aminosilicon compound. Said solvent can be any suitable liquid that will not react with the components of the reaction. Preferably the solvent is also a solvent for the organosilicon product of the reaction as well.

Examples of suitable solvents include, but are not limited to, hydrocarbons such as toluene, xylene, hexane, cyclohexane and heptane; halogenated hydrocarbons such as methylene chloride, chloroform, trichloroethylene and trichloroethane; and oxygenated compounds such as ethyl ether and ethyl acetate. Mixtures of two or more solvents can also be used, it only being required in this instance that the mixture, and not necessarily all the components in the mixture, be a solvent for the aminosilicon compound.

In the method of this invention the necessary components of the reaction mixture, i.e. the acyl halide, the aminosilicon compound, the aqueous solution of alkaline material and solvent, can be mixed in any manner as long as the acyl halide is added to the aminosilicon compound in the presence of the other two necessary components. In a preferred embodiment the acyl halide, or a solution thereof, is added to a well agitated mixture of aqueous alkaline material and solvent solution of aminosilicon material.

Except when the acyl halide is an acrylyl halide the method of this invention can be practiced at any reasonable temperature. Advantageously this method proceeds readily at room temperature. When an acrylyl halide is used this method should be practiced at as low a temperature as possible to minimize the formation of byproducts. Accordingly, when using the method of this invention to prepare acrylyl-substituted aminosilicon compounds, the reaction should be conducted at a temperature of from 0 to 10° C. Lower reaction temperatures are suitable provided the water does not freeze, but higher reaction temperatures will substantially reduce the yield of desired product.

The amounts of the necessary components to be used in this method are not narrowly critical, it only being necessary to have present a sufficient amount of alkaline material to neutralize all hydrogen halide as it is produced when the acyl halide reacts with the nitrogen-bonded hydrogen atoms and a sufficient amount of acyl halide to acylate every molecule of aminosilicon compound at least once.

Thus the alkaline material and the acyl halide are preferably used in equivalent amounts; e.g. one molecule of sodium hydroxide for every molecule of acrylyl chloride, although an excess of the alkaline material relative to the amount of hydrogen halide produced has not been found to be detrimental to the desired result of the reaction. A deficiency of alkaline material relative to the amount of hydrogen halide produced is to be avoided.

Also, the acyl halide and the aminosilicon compound should be used in equivalent amounts; e.g. one acrylyl chloride molecule for every molecule of aminosilicon compound which bears an acylatable amino group, although an excess of the acyl halide relative to acylatable amino groups has not been found to be detrimental to the desired result of the reaction. A deficiency of acyl halide, relative to the total number of acylatable amino groups, although merely leading to the preparation of incompletely acylated product when the acyl halide is free of aliphatic unsaturation, leads to products which can undergo a Michael-Addition type when the acyl halide contains aliphatic unsaturation. For this reason it is preferred, although not required, to fully acylate the aminosilicon compound when an acrylyl halide is used.

The amount of water that is used in the method of this invention should be sufficient to dissolve the alkaline material and, preferably, provide a less-than-saturated solution thereof. A 2% solution of sodium hydroxide has been found to be desirable.

The amount of solvent that is used in the method of this invention should be sufficient to dissolve the aminosilicon compound and, preferably, the organosilicon product as well.

During and after the addition of the acyl halide component to the aminosilicon component the reaction mixture should be thoroughly agitated to maintain an intimate contact between the aqueous and nonaqueous phases. The usual low shear means such as stirrers, paddles and impellers are sufficient to maintain sufficient agitation. Agitation is maintained until the acylation reaction is finished, typically within an hour.

After the reaction is finished and the organic phase has been isolated the product of the reaction can be separated from the solvent or allowed to remain in the solvent as desired. When acrylyl-substituted products are to be separated from the solvent it is desirable to add a polymerization inhibitor to the solution prior to any separating action such as distilling or fractionating.

The products of the method of this invention are useful as polar silicon-containing additives for cosmetic compositions, coating compositions, textile treating compositions and paints. The compositions of this invention are useful as comonomers with polymerizable vinyl monomers such as styrene, butadiene, methyl methacrylate, ethyl acrylate, vinyl acetate, vinyl chloride, vinylidene chloride and acrylonitrile. In particular the compounds of this invention bearing acrylylamine-substituted hydrocarbon radicals are useful as a reactive component in free radical curable compositions such as radiation curable compositions.

Thus, in a third aspect, this invention relates to a curable coating composition comprising an organosilicon compound containing at least one silicon-bonded acylamino-substituted hydrocarbon radical having the formula —QANQ'NAZ, wherein Z denotes H or R, R denotes a monovalent hydrocarbon radical, Q and Q' denote divalent hydrocarbon radicals, A denotes an acyl radical having the formula

$$CH_2=CBCO,$$

and B denotes H or $CH_3$, any remaining silicon-bonded radicals therein being selected from the group consisting of organic radicals and divalent oxygen atoms linking silicon atoms.

The curable compositions of this invention comprise a fully acrylylated diamine-substituted silicon compound which can be any of the compounds of this invention, including preferred embodiments thereof, delineated above.

In particular, curable compositions of this invention which are useful for coating a flexible substrate such as paper, polymer films and metal foils should comprise, as the acrylylated silicon compound, a fully acrylylated siloxane having the formula

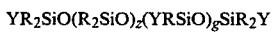
$$YR_2SiO(R_2SiO)_z(YRSiO)_gSiR_2Y$$

wherein Y and R have the meanings noted above, z has a value of from 10 to 2000 and g has a value of from 0 to 0.1 z. Preferably the siloxane having the above formula has a viscosity of from one hundred to ten thousand centistokes when the curable composition is to be used as a solventless coating composition.

Examples of siloxanes having the above formula include
$YMe_2SiO(Me_2SiO)_zSiMe_2Y$,
$Me_3SiO(Me_2SiO)_z(YMeSiO)_hSiMe_3$ and
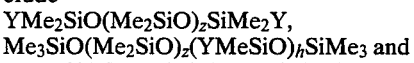
$YMe_3SiO(Me_2SiO)_z(YMeSiO)_hSiMe_2Y$, wherein h has a value of from greater than 0 to 0.1 z and z has the meaning noted above.

In the three formulae immediately above h has a value such that the siloxane contains at least one, and preferably at least two, acrylylamine-substituted hydrocarbon radicals.

The curable compositions of this invention consist of said fully acrylylated silicon compound, with or without the addition of curing agents. However, it is preferable to include therein a polymerization initiator such as a free radical generator or a photoinitiator to facilitate the curing thereof when the composition is to be cured by thermal and/or ultraviolet radiation. The particular initiator to be included depends upon the method to be used for curing the composition.

When the composition is to be cured by thermal means it is preferred that a free radical initiator be added to the curable composition. Examples of suitable free radical initiators include, but are not limited to, redox pairs, perborates, percarbonates, photochemical systems, azo compounds such as azo-bis(isobutyronitrile), acyl peroxides such as benzoyl peroxide, alkyl peroxides such as di-t-butyl peroxide and hydroperoxides such as cumene hydroperoxide.

When the composition is to be cured by ultraviolet radiation it is preferred that a photoinitiator be added to the composition. Examples of suitable photoinitiators include, but are not limited to, benzoin, benzoin alkyl ethers such as methyl, ethyl, isopropyl or isobutyl benzoin ether, acetophenone derivatives such as dialkoxyacetophenone such as diethoxyacetophenone, di- and trichloroacetophenones, $\alpha,\alpha$-dimethoxy-$\alpha$-phenylacetophenone, 1-hydroxycyclohexylphenyl ketone, 2-hydroxy-2-methyl-1-phenylpropane-1-one, methylphenyl glyoxylate, 4-benzoylbenzyl-trimethylammonium chloride, $\alpha$-acyloxime esters such as 1-phenyl-1,2- propanedione-2-(O -ethoxycarbonyloxime), thioxanthane and its derivatives, benzophenone in combination with a chain transfer agent such as a NH group and azo-bis(isobutyronitrile).

The reader is referred to any of the standard references that teach the polymerization of acrylyl-containing monomers. Included herein by reference are *Kirk-Othmer Encyclopedia of Chemistry and Technology;* John Wiley and Sons, N.J., Second Edition, 1972, Vol. I, pp. 274 to 284 and *Encyclopedia of Polymer Science and Technology;* John Wiley and Sons, N.J., 1966, Vol. I, pp. 177 to 197.

When the curable compositions of this invention are to be cured by electron beam radiation the addition of a polymerization initiator is not needed.

The curable compositions of this invention can further comprise optional components which are commonly used in curable silicon-containing compositions. Examples of said optional components include, but are not limited to, solvents such as those used to prepare the acrylylated silicon compound used therein, polymerizable vinyl monomers such as those delineated above, emulsion-forming components such as water and surfactants, colorants, stabilizers, fillers such as silica and carbon, adhesion promoters and surface modifiers such as lubricants and release agents.

The curable coating compositions of this invention thus have many of the utilities of curable compositions such as molding, encapsulating, sealing and coating. In particular they find utility for coating flexible substrates such as paper, metal foil, polymer films, optical fibers and textiles and relatively non-flexible substrates such as polymer laminates, such as circuit boards, siliceous substrates such as ceramic, glass and brick, wood substrates and molded, cast and stamped metal articles. The curable coatings of this invention are useful in the adhesive release art, the electronic art such as encapsulating and photoresist, the graphic art etc.

Thus, in a fourth aspect the present invention relates to a process for providing a cured silicon-containing coating on a substrate, said process comprising (A) applying the curable coating composition of this invention to the substrate and thereafter (B) curing the applied coating.

In the process of this invention the curable coating composition of this invention is applied to a substrate as a thin layer by any suitable manner such as brushing, spraying, rolling, dipping or spreading. By a thin layer it is meant from a monomolecular layer to a hundred mils. Curable coating compositions of this invention comprising siloxane compounds of this invention are typically applied in a layer having a thickness of from 0.01 to 100 mils.

The applied coating can be cured by any suitable means such as chemical, radiant or thermal means. As noted above, when the applied coating is to be cured by thermal or ultraviolet radiation, the applied composition should contain a polymerization initiator. In a preferred embodiment of this invention the applied composition is cured with electron beam radiation and the composition needs no added initiator.

As noted above, the coating composition of this invention can be applied to substrates of various compositions, shapes, sizes and uses. In a preferred embodiment of this process a flexible substrate is coated for the purpose of providing for the substrate an adhesive-releasing surface.

In the adhesive-releasing art a flexible substrate such as paper, polymer film, polymer-coated paper or metal foil is rendered adhesive-releasing by the application of a curable fluid composition to the flexible substrate at a coating weight of from 0.5 to 2 pounds per ream of substrate. After the applied composition has been cured the thus-treated surface is brought into adhesive contact with an adhesive, either free or disposed on a surface of an article. The adhesive-releasing surface thereby serves as a protective layer for one surface of the adhesive until the adhesive is to be used, whereupon it can be readily removed from the adhesive.

In the process of this invention there is provided a fast, clean, efficient process for providing an adhesive-releasing surface that is fully cured, non-transferring and stable when used with cast adhesives or supported adhesives and in an on-line, i.e. immediate adhesive coating, mode or in a conversion, i.e. delayed adhesive coating, mode.

The following examples are disclosed to further teach how to practice the invention in its several aspects and not to limit the invention which is properly delineated by the appended claims.

All parts, percentages and ratios are by weight unless otherwise stated. Me, Ph and Vi denote the methyl radical, phenyl and vinyl radical, respectively.

The state of cure of an adhesive-release coating was determined by the ruboff, migration and smear tests.

Smear of a coating was measured by lightly rubbing the coating with a finger and looking for hazing of the coating. The degree of haze (none, very slight, slight, moderate, gross) that was observed indicated the degree of smear of the coating. A fully cured coating shows no haze and therefore has no smear.

Ruboff of a coating was measured by vigorously rubbing the coating with the index finger tip, trying to remove the coating from the paper. The extent of ruboff was described as none, very slight, slight, moderate or gross. A fully cured coating demonstrates no ruboff.

Migration of a coating was measured by placing a test strip of No. 5910 3M ® (St. Paul, Minn.) brand transparent tape on the coating, adhesive-bearing surface in contact with the coating, and rubbing the strip 5 to 20 times with a finger to adhere it to the coating. The strip of transparent tape was then removed from the coating and its adhesive-bearing surface was doubled, end to end, onto itself and pressed firmly together. For a coating having no migration the force needed to separate the doubled test strip was approximately the same as the force needed to separate a doubled strip of unexposed tape. Other ratings include very slight, slight, moderate and gross migration. A fully cured coating demonstrates no migration.

Adhesive release for a coating was measured on a fully cured coating.

Each cured coating was prepared for release testing according to the following procedure. The cured coating was coated with adhesive using either a solution of Monsanto ® (St. Louis, Mo.) GMS-263 acrylic adhesive (hereinafter acrylic adhesive) or National Starch ® (New York, N.Y.) 36-6045 styrene-butadiene rubber adhesive (hereinafter SBR adhesive). The adhesive solution was applied to the cured coating at a wet thickness of 3 mils (76.2 $\mu$m) using a draw down bar. The applied adhesive was air-dried at room temperature for one minute, heated at 70° C. for one minute and then cooled to room temperature again for 1 minute. A sheet of 60 pound matte litho was applied to the dried adhesive and the resulting laminate was pressed with a 4.5 pound rubber coated roller.

Release testing of the laminates was accomplished by cutting the laminates into 1 inch (25.4 mm) strips and pulling the matte/adhesive laminate from the kraft paper/coating laminate at an angle of 180° at 400 inches/minute (0.17 m/s). The force, in grams per inch, that was required to separate the laminae was noted as adhesive release. This value was converted to newtons per meter (N/m) for this disclosure by multiplying by 0.3860885 in.N/g.m and rounding off to three significant figures.

TABLE I

| | $Me_3SiO(Me_2SiO)_x(MeYSiO)_ySiMe_3$ | | | |
|---|---|---|---|---|
| Compound | x | y | Y | A |
| Ia | 0 | 1 | $-CH_2CHCH_2NACH_2CH_2NAH$<br>$\|$<br>$CH_3$ | $CH_2=CHC=O$ |
| Ib | 0 | 1 | $-CH_2CHCH_2NACH_2CH_2NAH$<br>$\|$<br>$CH_3$ | $CH_3C=O$ |
| Ic | 0 | 1 | $-CH_2CHCH_2NACH_2CH_2NAH$<br>$\|$<br>$CH_3$ | $C_6H_5C=O$ |

TABLE I-continued

| Compound | x | y | Y | A |
|---|---|---|---|---|
| Id | 0 | 1 | $-CH_2CHCH_2NACH_2CH_2NAH$<br>$\quad\quad\quad\ \ \|$<br>$\quad\quad\quad\ CH_3$ | $CH_3CH_2CH_2\overset{\|}{C}=O$ |
| Ie | 93 | 5 | $-CH_2CHCH_2NACH_2CH_2NAH$<br>$\quad\quad\quad\ \ \|$<br>$\quad\quad\quad\ CH_3$ | $CH_2=CH\overset{\|}{C}=O$ |
| If | 117 | 6 | $-CH_2CHCH_2NACH_2CH_2NAH$<br>$\quad\quad\quad\ \ \|$<br>$\quad\quad\quad\ CH_3$ | $CH_2=CH\overset{\|}{C}=O$ |
| Ig | 95 | 3 | $-CH_2CHCH_2NACH_2CH_2NAH$<br>$\quad\quad\quad\ \ \|$<br>$\quad\quad\quad\ CH_3$ | $CH_2=CH\overset{\|}{C}=O$ |
| Ih | 90 | 8 | $-CH_2CHCH_2NACH_3$<br>$\quad\quad\quad\ \ \|$<br>$\quad\quad\quad\ CH_3$ | $CH_2=CH\overset{\|}{C}=O$ |
| Ii | 45.5 | 2.5 | $-CH_2CHCH_2NACH_2CH_2NAH$<br>$\quad\quad\quad\ \ \|$<br>$\quad\quad\quad\ CH_3$ | $CH_2=CH\overset{\|}{C}=O$ |

Header formula: $Me_3SiO(Me_2SiO)_x(MeYSiO)_ySiMe_3$

TABLE II

| Compound | Adhesive | Release Force, N/m |
|---|---|---|
| Ie | SBR | 19.3 to 27.0 |
| Ie | Acrylic | 25.1 to 38.6 |
| If | SBR | 15.4 to 25.1 |
| If | Acrylic | 19.3 to 42.5 |

TABLE III

Header formula: $YMe_2SiO(Me_2SiO)_x(MeYSiO)_ySiMe_2Y$

| Compound | x | y | Y |
|---|---|---|---|
| IIIa | 13 | 0 | $-CH_2CH_2CH_2NH\overset{O}{\overset{\|\|}{C}}CH=CH_2$ |
| IIIb | 13 | 0 | $-CH_2CHCH_2N\overset{O}{\overset{\|\|}{C}}CH=CH_2$<br>$\quad\quad\quad\ \|\quad\quad\|$<br>$\quad\quad\ CH_3\ \ CH_3$ |
| IIIc | 48 | 0 | $-CH_2CHCH_2NCH_2CH_2NH$<br>$\quad\quad\quad\ \|\quad\quad\quad\quad\ \ \|$<br>$\quad\quad\ CH_3\quad\quad\quad O=CCH=CH_2$<br>$CH_2=CH\overset{\|}{C}=O$ |
| IIId | 47 | 1 | $-CH_2CHCH_2NCH_2CH_2NH$<br>$\quad\quad\quad\ \|\quad\quad\quad\quad\ \ \|$<br>$\quad\quad\ CH_3\quad\quad\quad O=CCH=CH_2$<br>$CH_2=CH\overset{\|}{C}=O$ |

EXAMPLE 1

Preparation of Ia, Table I

A 250 ml three-necked flask fitted with a thermometer, dropping funnel and a magnetic stir bar, was charged with 100 ml of 2% sodium hydroxide solution and an aminosiloxane having the formula $(Me_3SiO)_2$-$Si(CH_3)CH_2CH(CH_3)CH_2NHCH_2CH_2NH_2$ (5 g, 14.9 mmols, 29.7 mmols of NH) in 60 ml of toluene. The reaction mixture was cooled externally and maintained at 0° C. Acrylyl chloride (2.7 g, 29.8 mmols) in 20 ml of toluene was added to the reaction mixture and stirred. After the addition, the mixture was stirred for another 15 minutes. The organic layer was separated, the aqueous layer was extracted with toluene and the combined organic layer was washed with water and dried over anhydrous $Na_2SO_4$. Solvent was removed on a rotary evaporator and the residue was dried under reduced pressure. An infrared spectrum of the compound showed absorptions at 3300 cm$^{-1}$ due to amide NH stretching vibration, at 1550 cm$^{-1}$ due to amide NH bending vibration, and at 1670–1620 cm$^{-1}$ due to amide carbonyl stretching vibrations. All these were absent in the starting aminosiloxane. A proton NMR spectrum showed absorptions at δ=6.6 to 5.55 as multiplets for $$C\underline{H}_2=C\underline{H}CON- \text{ and } C\underline{H}_2=C\underline{H}CONH \text{ protons.}$$

EXAMPLE 2

Preparation of Ib, Table I

In a 250 ml separatory funnel was taken 2.0 g (5.95 mmols, 11.9 mmols of NH) of the aminosiloxane used in Example 1, 30 ml of toluene and 0.74 g (18.6 mmols) of NaOH in 15 ml of water and ice cubes. To this 1.22 g (15.5 mmols) of acetyl chloride was added and the mixture was shaken for five minutes. Five drops of triethylamine were added to remove excess acetyl chloride and the mixture was shaken for another five minutes. The organic layer was separated, dried over anhydrous $Na_2SO_4$ and solvent was removed to obtain the product. A proton NMR spectrum showed singlets for

and —NHCOC$H_3$ protons at δ=2.2 and 2.0. An infrared spectrum showed absorptions at 3300 cm$^{-1}$ for amide NH stretching vibration, amide carbonyl stretching absorption at 1680–1620 cm$^{-1}$, and amide NH bending vibration at 1550 cm$^{-1}$.

EXAMPLE 3

Preparation of Ic, Table I

In a 250 ml separatory funnel was taken 2.0 g (5.95 mmols, 11.9 mmols of NH) of the aminosiloxane used in Example 1, 30 ml of chloroform, 0.69 g (17 mmols) of NaOH dissolved in 15 ml of water and a few ice cubes. To this 2.64 g (14.3 mmols) of benzoyl bromide was added. The mixture was shaken for five minutes. Five drops of triethylamine were added to the above mixture and shaken for another five minutes. The organic layer was separated, dried over anhydrous $Na_2SO_4$ and solvent was removed to obtain the product. An infrared spectrum showed absorptions at 3350 cm$^{-1}$ due to amide NH stretching vibration, at 1670–1620 cm$^{-1}$ due to amide carbonyl group and at 1790, 1730, 1600 and 1580 cm$^{-1}$ for aromatic C≡C.

EXAMPLE 4

Preparation of Id, Table I

Example 3 was repeated except 1.52 g (14.4 mmols) of butyryl chloride was used in place of the benzoyl bromide. An infrared spectrum showed absorptions at 3300 cm$^{-1}$ due to amide NH stretching vibration, at 1670 to 1630 cm$^{-1}$ due to amide carbonyl stretching and at 1540 cm$^{-1}$ due to amide NH bending vibrations.

A proton NMR spectrum showed resonances at $\delta = 2.5$ to 2.1 as multiplets due to

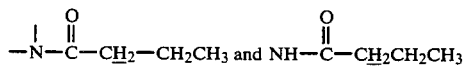

protons, at $\delta = 1.9-1.5$ due to

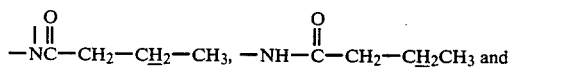

protons; at $\delta = 1.2$ to 0.9 due to

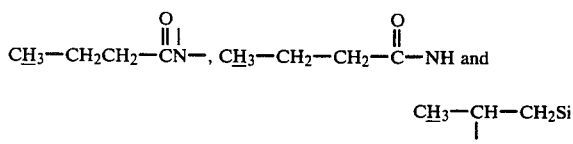

protons.

EXAMPLE 5

Preparation of Ie, Table I

A one liter three-necked flask, fitted with a thermometer, stirring paddle and a dropping funnel was charged with 100 g (0.119 mol of NH) of an aminosiloxane having an amine neutral equivalent of 840, a viscosity of 172 cs and the nominal formula $Me_3SiO(Me_2SiO)_{93}$-$(MeYSiO)_5SiMe_3$ (Y'=CH$_2$CH(CH)CH$_2$NHCH$_2$CH$_2$NH$_2$) and 350 ml of chloroform. The mixture was cooled to approximately 0° C. Sodium hydroxide (6.9 g, 0.17 mol) dissolved in 80 ml of water was added to the above reaction mixture. While maintaining the temperature at approximately 0° C., 12.9 g (0.143 mol) of CH$_2$=CHCOCl was added and the mixture was stirred for five minutes. The organic phase was separated, washed with water, dried over anhydrous $Na_2SO_4$ and decanted. To this 5 ml of ethanol, 100 ppm of hydroquinone and 20 ppm of phenothiazine were added and solvent was removed under reduced pressure. The product had a viscosity of 2187 cs at 25° C. The infrared spectrum showed —NH stretching vibration at 3300 cm$^{-1}$; —NH bending vibration at 1550 cm$^{-1}$; carbonyl stretching at 1680–1630 cm$^{-1}$; and bending vibration for conjugated carbon-carbon double bond at 1610 cm$^{-1}$. All the above infrared absorptions were absent in the original aminoalkyl-substituted organopolysiloxane. Starting and final organopolysiloxanes also showed absorption bands at 1120–1010 cm$^{-1}$ for siloxane linkages. A proton NMR spectrum of the product showed absorptions at $\delta = 6.7$ to 5.5 as multiplets due to CH$_2$=CH protons; and at $\delta = 3.8-3.2$ due to

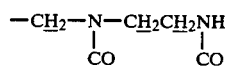

protons. In the aminoalkyl-substituted organopolysiloxanes absorptions at $\delta = 6.7$ to 5.5 were absent and the

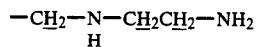

protons absorbed at $\delta = 2.8$ to 2.4. The product had the nominal structure shown in Table I.

EXAMPLE 6

Preparation of If, Table I

A one liter three-necked flask, fitted with a thermometer, stirring paddle and a dropping funnel was charged with 100 g (0.126 mol of NH) of an aminosiloxane having an amine neutral equivalent of 793, a viscosity of 172 cs and the nominal formula $Me_3SiO(Me_2SiO)_{117}(MeY'$-$SiO)_6SiMe_3$, (Y'=CH$_2$CH(CH$_3$)CH$_2$NHCH$_2$CH$_2$NH$_2$), and 350 ml of chloroform. The mixture was cooled to approximately 0° C. Sodium hydroxide (6.7 g, 0.1675 mol) dissolved in 80 ml of water was added to the above reaction mixture. While maintaining the temperature between 0° and 5° C., 13.65 g (0.1513 mol) of CH$_2$=CHCOCl was gradually added with stirring. Once the addition was over, the mixture was stirred for an additional 10 minutes, the organic phase was separated, dried over anhydrous $Na_2SO_4$ and decanted. To this 3 ml of ethanol, 100 ppm of hydroquinone and 20 ppm of phenothiazine were added and solvent was removed under reduced pressure. The product had a viscosity of 3506 cs at 25° C. The infrared spectrum and proton NMR spectrum were similar to that of Ie.

EXAMPLE 7

Paper Coating, Electron Beam Curing and Adhesive Release Testing.

The organopolysiloxanes Ie and If described in Examples 5 and 6 undergo free radical initiated crosslinking. Hence these materials can be crosslinked by electron beam irradiation under an inert atmosphere. For example, the silicone fluids Ie and If were separately coated onto supercalendered kraft paper, and low and high density polyethylene and cured under electron beam radiation (Energy Sciences Lab Model Electrocurtain CB 150/15/10L). Curing to no smear, no migration and no ruboff was achieved at 2 Mrad dosage under inert atmosphere. The accelerating voltage was kept between 150-160 kilovolts. Quantitative measurements of the release properties of cured film of these new compositions on supercalendered kraft paper were also obtained. The release force measurements thus obtained are summarized in Table II.

EXAMPLE 8

Paper Coating, UV Curing and Adhesive Release Testing

Ie was mixed with 5 wt % of a 50/50 mixture of benzophenone and 1-hydroxycyclohexylphenyl ketone as a photoinitiator. The mixture was coated onto kraft paper at a coating weight of 0.5 to 1 pound per ream and the coating was irradiated for about 3 seconds at a distance of 2 to 3 inches with the ultraviolet light from 2 medium pressure mercury vapor lamps having output of 200 watts/inch.

The thus-cured coating was immediately laminated with SBR adhesive. The release force of the laminate, as measured by the release test noted above, was 42.5 N/m.

The lamination was also done with acrylic adhesive and a release force of 67.6 N/m was observed.

EXAMPLE 9

Preparation and Use of Ig, Table I

A 250 ml three-necked flask, fitted with a thermometer, stirring paddle and a dropping funnel was charged with 20 g (0.015 mol of NH) of an aminosiloxane having an amine neutral equivalent of 1337, the nominal formula $$Me_3SiO(Me_2SiO)_{95}(MeY'SiO)_3SiMe_3$$
$$(Y'=CH_2CH(CH_3)CH_2NHCH_2CH_2NH_2)$$

and a viscosity of 127 cs and 100 ml of ether. The mixture was cooled to approximately 0° C. Sodium hydroxide (0.72 g, 0.018 mol) dissolved in 40 ml of water was added to the above reaction mixture. While maintaining the temperature at approximately 0° C., 1.4 g (0.0155 mol) of acrylyl chloride was added and the mixture stirred for five minutes. The organic phase was separated, washed with water, dried over anhydrous Na$_2$SO$_4$ and decanted. To this, 100 ppm of hydroquinone was added and solvent was removed under reduced pressure. The infrared spectrum showed —NH stretching vibration at 3300 cm$^{-1}$; —NH bending vibration at 1550 cm$^{-1}$; carbonyl stretching at 1680–1630 cm$^{-1}$; conjugated olefinic CH stretching at 3030 cm$^{-1}$; and bending vibration for conjugated carbon-carbon double bond at 1610 cm$^{-1}$. All the above infrared absorptions were absent in the original alkylaminofunctional organopolysiloxane. Starting and final organopolysiloxanes also showed absorption bands at 1120–1010 cm$^{-1}$ for siloxane linkages. An $^1$H NMR spectrum of the amide showed absorptions at δ=6.7 to 5.5 as multiplets due to acrylic CH$_2$=CH protons; and at δ=3.8–3.2 due to

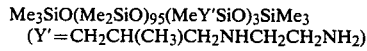

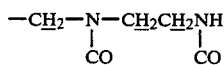

protons. In the alkylaminofunctional polysiloxanes absorptions at δ=6.7 to 5.5 were absent and the —CH$_2$—N—CH$_2$CH$_2$—NH$_2$ protons absorbs at δ=2.8 to 2.4.

The above fluid was mixed with 5 wt % of the photoinitiator used in Example 8, coated on supercalendered kraft sheet and on polyethylene-coated kraft sheet and cured under two 200w/inch medium pressure mercury lamp at 30–40 ft/min. They were laminated with adhesive and release force was determined.

The coated supercalendered kraft substrate released acrylic adhesive with a force of 48.3 N/m and SBR adhesive with a force of 27 N/m.

The coated polyethylene coated kraft released acrylic adhesive with a force of from 29.0 to 38.6 N/m.

EXAMPLE 10

Preparation and Use of Ih, Table I

A 500 ml three-necked flask, equipped with a thermometer, stirring paddle and a dropping funnel was charged with 40 g (39.2 mmols of NH) of an aminosiloxane having an amine neutral equivalent of 1002, a viscosity of 146 cs and a nominal formula Me$_3$SiO(Me$_2$SiO)$_{90}$(meY'SiO)$_8$SiMe$_3$ (Y=—CH$_2$CH(CH$_3$)CH$_2$NHCH$_3$) and 150 ml of chloroform. This was cooled to 0° C. Sodium hydroxide (2.3 g, 57.6 mmols) dissolved in 40 ml of water was added to the above mixture. The reaction mixture was agitated, maintaining the temperature at 0° C., and 4.32 g (48.0 mmols) of acrylyl chloride was added gradually. After the addition, the mixture was stirred for five minutes, the organic layer was separated, dried over anhydrous Na$_2$SO$_4$ and solvent was removed. The product had an amine neutral equivalent of 128535 indicating that the 99.2% of the amine was acylated. An infrared spectrum showed absorptions at 1660 cm$^{-1}$ due to

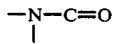

stretching vibration, carbon-carbon double bond stretch at 1620 cm$^{-1}$, and Si-O stretching at 1110–1020 cm$^{-1}$. A proton NMR spectrum showed multiplets at δ=6.6–5.5 due to CH$_2$=CH—CO protons.

This organopolysiloxane was coated on polyethylene coated kraft paper using a lab blade coater, and cured under 5 Mrad of electron-beam radiation to a smear, migration and ruboff-free coating.

EXAMPLE 11

Preparation and Use of Ii, Table I

A one liter three-necked flask, fitted with a thermometer, stirring paddle and a dropping funnel was charged with 100 g (0.127 mol of NH) of an aminosiloxane having a viscosity of 72 cs, an amine neutral equivalent of 785 and the nominal formula Me$_3$SiO(Me$_2$SiO)$_{45.5}$(MeY'SiO)$_{2.5}$SiMe$_3$ (Y'=—CH$_2$CH(CH$_3$)CH$_2$NHCH$_2$CH$_2$NH$_2$) and 350 ml of chloroform. The mixture was cooled to approximately 0° C. Sodium hydroxide (6.7 g, 0.17 mol) dissolved in 80 ml of water was added to the above reaction mixture while maintaining the temperature at approximately 0° C., 13.8 g (0.153 mol) of acrylyl chloride was added and the mixture was stirred for five minutes. The organic phase was separated, washed with water, dried over anhydrous Na$_2$SO$_4$ and decanted. To this 5 ml of ethanol, 100 ppm of hydroquinone and 20 ppm of phenothiazine were added and solvent was removed under reduced pressure.

Using a lab blade coater, this organopolysiloxane was coated onto polyethylene coated kraft paper and was found to cure to give a migration-, smear- and ruboff-free coating at 2 Mrad dosage.

EXAMPLES 12 and 13

Preparation of Ii, Table I

Following the procedure of Example 11, except either ethyl ether, or ethyl acetate was used as the solvent, instead of chloroform, the same polymer was formed.

EXAMPLE 14

Preparation and Use of IIIa, Table III

A 250 ml three-necked flask, fitted with a thermometer, dropping funnel and a magnetic stirrer was charged with 20 g (32.9 mmols of NH) of an aminosiloxane having a viscosity of 16 cs at 25° C., an amine neutral equivalent of 608 and the formula $Y'Me_2SiO(Me_2SiO)_{1.3}SiMe_2Y'$ ($Y' = -CH_2CH_2CH_2NH_2$) and 80 ml of chloroform. The mixture was stirred and cooled to approximately 0° C. To this 1.82 g (45.5 mmols) of sodium hydroxide dissolved in 25 ml of $H_2O$ was added. Acrylyl chloride (3.4 g; 37.8 mmols) dissolved in 5 ml of chloroform was added to the above reaction mixture at 0° C. The mixture was stirred for another five minutes, the layers were separated. The chloroform solution was dried over anhydrous $Na_2SO_4$, decanted and 1 ml of ethanol, 100 ppm hydroquinone and 20 ppm phenothiazine were added to it and solvent removed under reduced pressure to obtain 19 g (87%) of IIIa.

An infrared spectrum showed absorptions at 3280 $cm^{-1}$ due to amide NH stretching vibrations, at 1660 $cm^{-1}$ due to amide carbonyl stretching vibration, at 1550 $cm^{-1}$ due to amide NH bending vibrations. Starting amino fluid and final acrylamide fluid also showed absorption at 1100 to 1010 $cm^{-1}$ due to siloxane.

The above fluid was mixed with 5 wt % of the photoinitiator used in Example 8, coated on supercalendered kraft paper and cured under two 200 w/inch medium pressure mercury lamps at a speed of 20 ft/min to obtain a smear-free coating.

EXAMPLE 15

Preparation of IIIb, Table III

A 500 ml three-necked flask equipped with a thermometer, stirring paddle and a dropping funnel was charged with 50 g (61.8 mmols of NH) of an aminosiloxane having an amine neutral equivalent of 809, a viscosity of 25 cs and the formula $Y'Me_2SiO(Me_2SiO)_{1.3}SiMe_2Y'$ ($Y' = -CH_2CH(CH_3)CH_2NHCH_3$), 150 ml of trichloroethylene and 2.99 g (74.8 mmols) of NaOH in 60 ml of water. The reaction mixture was cooled to 0° C. and acrylyl chloride 6.13 g (68 mmols) was slowly added maintaining the temperature between 0° and 5° C. After addition was over, the stirring continued for a few minutes. The organic layer was separated. To the organic layer 2 ml of tetrahydrofuran and 100 ppm hydroquinone were added. Solvent was removed and the fluid filtered to remove any residual sodium chloride. The product had a viscosity of 48 cs at 25° C. An infrared spectrum showed carbonyl stretching vibration at 1655 $cm^{-1}$ and carbon-carbon double bond stretch at 1620 $cm^{-1}$. The starting and final fluid also showed absorptions at 1110 to 1020 $cm^{-1}$ for SiOSi linkage.

EXAMPLE 16

Preparation of IIIc, Table III

A 500 ml four-necked flask equipped with an air stirrer, thermometer, condenser and $N_2$ inlet was charged with 181.52 g of polydimethylsiloxane, 2.45 mols of $Me_2SiO$ units, 18.48 g (0.051 mol) of

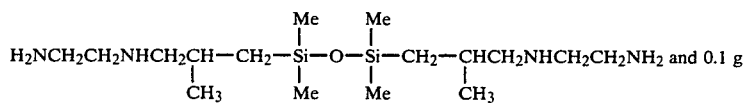

(0.00178 mol) of potassium hydroxide. The above were heated and maintained at 149°–152° C. for 4½ hours. After this the reaction mixture was cooled to room temperature and KOH was neutralized. This fluid had a viscosity of 82 cs at 25° C. and an amine neutral equivalent of 1071.

A one liter three-necked flask equipped with a thermometer, stirring paddle and a dropping funnel was charged with 100 g of the above organopolysiloxane (93.4 mmols of NH) and 350 ml of chloroform and 4.93 g (123.25 mmols) of sodium hydroxide in 80 ml of water. The above reaction mixture was cooled to 0° C. Acrylyl chloride 10.1 g (112 mmols) was added to the above mixture, while maintaining the temperature between 0°–5° C. After the addition, the mixture was stirred for five minutes. The organic layer was separated and 4 ml of ethanol and 100 ppm hydroquinone were added to it. Solvent was removed under reduced pressure. The product had a viscosity of 1096 cs at 25° C. The infrared spectrum showed absorptions for —NH stretching at 3300 $cm^{-1}$; —NH bending vibration at 1550 $cm^{-1}$; carbonyl stretching at 1650 $cm^{-1}$; and bending vibration for conjugated carbon-carbon double bond at 1610 $cm^{-1}$. All the above absorptions were absent on the original alkylaminofunctional organopolysiloxane. Starting and final organopolysiloxanes also showed absorption bands at 1120 to 1020 $cm^{-1}$ for siloxane linkages.

EXAMPLE 17

Preparation and Peroxide Curing of IIId, Table III

A 1 liter four-necked flask equipped with a stirring paddle, thermometer, condensed and a $N_2$ inlet was charged with 433.3 g of polydimethylsiloxane, 5.84 mos of $Me_2SiO$ units, 45.05 g (0.124 mol) of

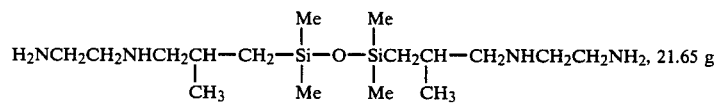

of polymethylaminoalkylsiloxane, 0.12 mol of MeY'SiO units (Y'=—CH₂CH(CH₃)CH₂NHCH₂CH₂NH₂) and 0.25 g (0.004 mol) of KOH. The mixture was heated at 149°–152° C. for ~3 hours, after which another 0.26 g (0.0046 mol) of KOH was added and heating continued for another five hours. The mixture was then cooled to room temperature and the KOH was neutralized. This aminoalkylorganopolysiloxane had a viscosity of 86 cs at 25° C. and an amine neutral equivalent of 709.

A 1 liter three-necked flask, fitted with a thermometer stirring paddle and a dropping funnel was charged with 100 g (0.141 mol of amine) of the above organopolysiloxane, 350 ml of chloroform and 8.16 g (0.204 mol) of sodium hydroxide in 75 ml of water. The above mixture was cooled to 0° C. and 15.3 g (0.17 mol) of acrylyl chloride was added to it, maintaining the temperature between 0° C. and 5° C. After the addition of acrylyl chloride the reaction mixture was stirred for another five minutes. The organic layer was separated, 3 ml of ethanol and 100 ppm hydroquinone were added to it, solvent was removed under reduced pressure to obtain the product having a viscosity of 1558 cs at 25° C. The infrared spectrum showed absorptions at 3300 cm⁻¹ due to amide

stretching vibration; amide

bending vibration at 1550 cm⁻¹, carbonyl stretching vibration at 1680–1630 cm⁻¹.

All the above absorptions were absent in the original polysiloxanes. A proton NMR spectrum showed absorptions at δ=6.6–5.5 as multiplets due to acrylic CH₂=CH protons.

A small portion of the above fluid was mixed with 5% by weight of benzoyl peroxide and this was coated on aluminum and glass sheets and was cured by heating to 150° C. for 2 minutes.

EXAMPLE 18

A 500 ml three-necked flask fitted with a thermometer, magnetic stirring bar and an addition funnel was charged with 50 g (0.062 mol of amine) of an aminofunctional organopolysiloxane having an amine neutral equivalent of 805, a viscosity of 98 cs and a nominal formula Me₃SiO(Me₂SiO)₆₉.₂₅(MeY'SiO)₃.₇₅SiMe₃

(Y'=CH₂CH(CH₃)CH₂NHCH₂CH₂NH₂);

and 200 ml of trichloroethylene. The mixture was cooled to approximately 0° C. Sodium hydroxide (3.9 g, 98 mmols) dissolved in 50 ml of water was added to the above reaction mixture. A mixture of acrylyl chloride (29.7 mmols, 2.67 g), benzoyl bromide (29.7 mmols, 5.50 g) and acetyl chloride (29.7 mmols, 2.33 g) dissolved in 20 ml of trichloroethylene was gradually added to the above stirred reaction mixture. Care was taken to maintain the temperature between −5° and +2° C. After the addition of acid halides, the reaction mixture was stirred for another five minutes. To the above mixture five drops of triethylamine was added in order to enhance the hydrolysis of the unreacted acid halides and the mixture was stirred for an additional five minutes. The organic phase was separated and stabilized with 1 ml of THF and 100ppm of hydroquinone. Solvent was removed under reduced pressure to obtain the product. The product had a viscosity of 398.8 cs at 25° C. Infrared spectrum showed stretching vibration due to amide

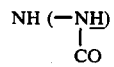

at 3320 cm⁻¹; amide carbonyl stretching vibrations

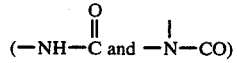

at 1670–1620 cm⁻¹; amide

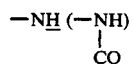

bending vibration at 1555–1540 cm⁻¹. Besides, the starting and final fluid had absorptions at 1120–1020 cm⁻¹ due to —SiO—Si— linkage. Proton NMR spectra showed resonances at 7.3 ppm due to aromatic protons, at 6.5–5.5 ppm due to acrylic protons

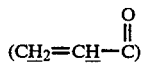

and at 2.2 and 2.0 ppm due to acetyl (CH₃—CO—) protons. Hence the product has the following nominal formula

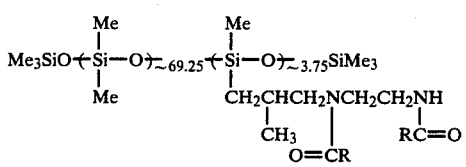

where R=CH₃—, C₆H₅ or CH₂=CH—.

That which is claimed is:

1. An organosilicon compound containing at least one silicon-bonded acylamino-substituted hydrocarbon radical having the formula —QNAQ'NAZ, wherein Z denotes H or R, R denotes a monovalent hydrocarbon radical, Q and Q' denote divalent hydrocarbon radicals, A denotes an acyl radical having the formula

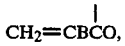

and B denotes H or CH₃, any remaining silicon-bonded radicals therein being selected from the group consisting of organic radicals and divalent oxygen atoms linking silicon atoms.

2. An organosilicon compound according to claim 1 having the average unit formula $R_c(NHAQ'NAQ)_dSiO_{(4-c-d)/2}$, wherein c has a value of from 0 to 3, d has a value of from >0 to 4, and c+d has a value of from 1 to 4.

3. An organosilicon compound according to claim 2 having the formula $YR_2SiO(R_2SiO)_x(YRSiO)_ySIR_2Y$ wherein Y denotes R or $-QNACH_2CH_2NAH$, x has a value of from 0 to 5000 and y has a value of from 0 to 500.

4. An organosilicon compound according to claim 2 having the formula $(R)_eSi(QNACH_2CH_2NAH)_{4-e}$ wherein e has a value of 0, 1, 2 or 3.

5. An organosilicon compound according to claim 2 wherein R is selected from the group consisting of methyl, phenyl and vinyl.

6. A method for preparing an organosilicon compound containing at least one silicon-bonded acylamino-substituted hydrocarbon radical, said method comprising (I) admixing (i) a composition comprising an acyl halide to (ii) a composition comprising an aminosilicon compound having at least one silicon-bonded amino-substituted hydrocarbon radical containing at least one nitrogen-bonded hydrogen, all other silicon valences therein being satisfied by radicals selected from the group consisting of organic radicals and divalent oxygen atoms linking silicon atoms, said admixing being done in the presence of (iii) an aqueous solution of a water-soluble alkaline material and (iv) a water-insoluble solvent for (ii), the amounts of components (i), (ii) and (iii) being sufficient to acylate at least one amino nitrogen atom containing at least one nitrogen-bonded hydrogen atom per molecule of aminosilicon compound and to provide at least an equivalent amount of alkaline material relative to the amount of acyl halide, and thereafter (II) agitating the mixture comprising (i) and (ii) until the compound is formed.

7. A method according to claim 6 wherein the silicon-bonded amino-substituted hydrocarbon radical has the formula $-Q(NHQ')_aNZH$ and the acyl halide has the formula $R''COX$, wherein
Q and Q' denote divalent hydrocarbon radicals,
R'' denotes a substituted or unsubstituted monovalent hydrocarbon radical,
X denotes a halogen atom,
Z denotes hydrogen or a monovalent hydrocarbon radical and a has a value of 0 or 1.

8. A method according to claim 7 wherein the acyl halide comprises a compound selected from the group consisting of $CH_2=CHCOCl$ and $CH_2=C(CH_3)COCl$.

9. A method according to claim 8 wherein the aminosilicon compound has the average unit formula $R_c(NH_2(Q'NH)_aQ)_dSiO_{(4-c-d)/2}$ wherein
R denotes a monovalent hydrocarbon radical,
c has a value of from 0 to 3,
d has a value of >0 to 4, and
c+d has a value of 1 to 4.

10. A method according to claim 9 wherein the aminosilicon compound is a siloxane having the formula $Y'R_2SiO(R_2SiO)_x(Y'RSiO)_ySiR_2Y'$ wherein
Y' denotes R or $-QNHCH_2CH_2NH_2$,
x has a value of from 0 to 5000 and
y has a value of from 0 to 500.

11. A method according to claim 9 wherein the aminosilicon compound is a silane having the formula $R_eSi(QNHCH_2CH_2NH_2)_{4-e}$ wherein e has a value of 0, 1, 2, or 3.

12. A method according to claim 9 wherein R is selected from the group consisting of methyl, phenyl and vinyl.

13. A method according to claim 6 wherein the alkaline material is an alkali metal hydroxide.

14. A method according to claim 6 wherein component (i) is admixed to a mixture of components (ii), (iii), and (iv).

15. A method according to claim 6 further comprising (III) isolating the organosilicon compound containing at least one silicon-bonded acylamino-substituted hydrocarbon radical.

16. A method according to claim 6 wherein the acyl halide comprises a compound selected from the group consisting of $CH_2=CHCOCl$ and $CH_2=C(CH_3)COCl$.

17. A method according to claim 6 wherein said admixing and said agitating is done at a temperature of from 0 to 10° C.

18. A method according to claim 8 wherein said admixing and said agitating is done at a temperature of from 0° to 10° C.

19. A method according to claim 15 wherein said admixing and said agitating is done at a temperature of from 0 to 10° C.

20. A curable coating composition comprising an organosilicon compound containing at least one silicon-bonded acylamino-substituted hydrocarbon radical having the formula $-QANQ'NAZ$, wherein Z denotes H or R, R denotes a monovalent hydrocarbon radical, Q and Q' denote divalent hydrocarbon radicals, A denotes an acyl radical having the formula

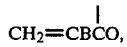

and B denotes H or $CH_3$, any remaining silicon-bonded radicals therein being selected from the group consisting of organic radicals and divalent oxygen atoms linking silicon atoms.

21. A curable coating composition according to claim 20 further comprising a polymerization initiator.

22. A curable coating composition according to claim 20 wherein the organosilicon compound has the formula $YR_2SiO(R_2SiO)_z(YRSiO)_gSiR_2Y$ wherein Y denotes R or $-QNACH_2CH_2NAH$, z has a value of from 10 to 2000 and g has a value of from 0 to 0.1z.

23. A curable composition according to claim 22 further comprising a polymerization initiator.

24. A curable coating composition according to claim 22 wherein each R denotes the methyl radical.

25. A curable coating composition according to claim 24 wherein the organosilicon compound has the formula $Me_3SiO(Me_2SiO)_z(YMeSiO)_hSiMe_3$ and h has a value of from greater than zero to 0.1z.

26. A curable coating composition according to claim 24 wherein the organosilicon compound has the formula $YMe_2SiO(Me_2SiO)_zSiMe_2Y$.

27. A curable coating composition according to claim 24 wherein the organosilicon compound has the formula $YMe_2SiO(Me_2SiO)_z(YMeSiO)_hSiMe_2Y$ and h has a value of from greater than zero to 0.1z.

28. A process for providing a cured silicon-containing coating on a substrate, said process comprising (A) applying the curable coating composition of claim 20 to the substrate and thereafter (B) curing the applied coating.

29. A process according to claim 28 wherein said curing is done by exposing the applied coating to a free radical generating means.

30. A process according to claim 28 wherein said curing is done by exposing the applied coating to electron beam radiation.

31. A process according to claim 28 wherein said curing is done by exposing the applied coating to ultraviolet radiation.

32. A process for providing a cured silicone coating on a substrate, said process comprising (A) applying the curable coating composition of claim 22 to the substrate and thereafter (B) curing the applied coating.

33. A process according to claim 32 wherein said curing is done by exposing the applied coating to a free radical generating means.

34. A process according to claim 32 wherein said curing is done by exposing the applied coating to electron beam radiation.

35. A process according to claim 32 wherein said curing is done by exposing the applied coating to ultraviolet radiation.

* * * * *